United States Patent
Douk et al.

[11] Patent Number: 5,827,241
[45] Date of Patent: Oct. 27, 1998

[54] RAPID EXCHANGE GUIDEWIRE MECHANISM

[75] Inventors: Nareak Douk, Lowell; Richard A. Gambale, Tyngsboro; William A. Berthiaume, Hudson, all of Mass.

[73] Assignee: C. R. Bard, Inc., Murray Hill, N.J.

[21] Appl. No.: 479,680

[22] Filed: Jun. 7, 1995

[51] Int. Cl.⁶ .................................................. A61M 25/00
[52] U.S. Cl. ........................... 604/280; 600/434; 600/585
[58] Field of Search .............................. 604/280, 96, 170, 604/282, 283, 284; 128/772, 657; 600/585, 434

[56] References Cited

U.S. PATENT DOCUMENTS

| | | |
|---|---|---|
| Re. 34,466 | 12/1993 | Taylor et al. . |
| 3,452,742 | 7/1969 | Muller ..................................... 128/657 |
| 3,774,605 | 11/1973 | Jewett . |
| 4,215,703 | 8/1980 | Willson ................................... 128/772 |
| 4,401,433 | 8/1983 | Luther . |
| 4,616,648 | 10/1986 | Simpson . |
| 4,748,982 | 6/1988 | Horzewski et al. . |
| 4,762,129 | 8/1988 | Bonzel . |
| 4,799,496 | 1/1989 | Hargreaves et al. . |
| 4,827,941 | 5/1989 | Taylor et al. . |
| 4,884,573 | 12/1989 | Wijay et al. . |
| 4,917,103 | 4/1990 | Gambale et al. ......................... 128/772 |
| 4,958,642 | 9/1990 | Christian et al. . |
| 4,961,433 | 10/1990 | Christian . |
| 5,031,636 | 7/1991 | Gambale et al. . |
| 5,045,061 | 9/1991 | Seifert et al. . |
| 5,113,872 | 5/1992 | Jahrmarkt et al. . |
| 5,117,838 | 6/1992 | Palmer et al. . |
| 5,131,407 | 7/1992 | Ischinger et al. . |
| 5,167,239 | 12/1992 | Cohen . |
| 5,211,183 | 5/1993 | Wilson ..................................... 128/772 |
| 5,234,407 | 8/1993 | Teirstein et al. . |
| 5,246,009 | 9/1993 | Adams . |
| 5,269,757 | 12/1993 | Fagan et al. . |
| 5,269,759 | 12/1993 | Hernandez et al. . |
| 5,271,415 | 12/1993 | Foerster et al. . |
| 5,290,232 | 3/1994 | Johnson et al. . |
| 5,290,247 | 3/1994 | Crittenden . |
| 5,318,527 | 6/1994 | Hyde et al. . |
| 5,318,541 | 6/1994 | Viera et al. . |
| 5,330,499 | 7/1994 | Kanesaka . |
| 5,344,413 | 9/1994 | Allman et al. . |
| 5,346,498 | 9/1994 | Greelis et al. . |
| 5,379,779 | 1/1995 | Rowland et al. . |
| 5,383,853 | 1/1995 | Jung et al. . |
| 5,388,590 | 2/1995 | Horrigan et al. . |
| 5,389,087 | 2/1995 | Miraki . |
| 5,389,100 | 2/1995 | Bacich et al. . |
| 5,395,332 | 3/1995 | Ressemann et al. . |
| 5,395,334 | 3/1995 | Keith et al. . |
| 5,395,389 | 3/1995 | Patel . |
| 5,404,886 | 4/1995 | Vance . |
| 5,404,888 | 4/1995 | Kontos et al. . |
| 5,497,782 | 3/1996 | Fugoso ..................................... 128/772 |
| 5,542,434 | 8/1996 | Imran . |
| 5,617,875 | 4/1997 | Schwager ................................. 128/772 |

FOREIGN PATENT DOCUMENTS

| | | |
|---|---|---|
| 0416734 | 3/1991 | European Pat. Off. . |
| 0415332 | 6/1991 | European Pat. Off. . |
| 0532109 | 3/1993 | European Pat. Off. . |
| 0534747 | 3/1993 | European Pat. Off. . |
| 2269539 | 2/1994 | United Kingdom . |
| WO9510976 | 4/1995 | WIPO . |

*Primary Examiner*—Corrine M. McDermott
*Assistant Examiner*—Cris L. Rodriguez
*Attorney, Agent, or Firm*—Arthur Z. Bookstein; John F. Perullo

[57] ABSTRACT

A method and apparatus are provided for withdrawing an indwelling over-the-wire catheter from an indwelling guidewire in which the guidewire is of a conventional length and is maintained in its indwelling position as the catheter is withdrawn. The position of the guidewire is maintained by constraining a segment of the catheter shaft and its included guidewire in a non-linear configuration such that the guidewire remains in its position as the catheter is withdrawn. The invention may be used to perform catheter exchanges without requiring the use of exchange wires, extension wires, rapid exchange catheters or special devices to connect the guidewire to the guide catheter.

19 Claims, 7 Drawing Sheets

RAPID EXCHANGE GUIDEWIRE MECHANISM

FIELD OF THE INVENTION

This invention relates to medical guidewires and catheters and to improved methods and devices to facilitate procedures involving their use.

BACKGROUND OF THE INVENTION

A wide variety of medical catheterization procedures involve the cooperative use of a guidewire over which the catheter can be threaded so that the guidewire can guide the catheter to the intended site in the patient's body. The use of a guidewire reduces the risk of trauma to the blood vessel by the advancing catheter and enables the catheter to be advanced quickly, thereby reducing the time required for the procedure. The guidewire typically is more readily manipulated by the physician into a desired position in the patient's body than is the far more flexible catheter. After the guidewire has been directed to the desired location in the body, the catheter then can be threaded over and along the guidewire, with the wire providing support and guidance for the flexible catheter.

Guidewires are used frequently in connection with catheters adapted for the diagnosis or treatment of the cardiovascular system. They are useful particularly in connection with those procedures where it may be necessary for the physician to use a series of different catheters that are inserted into and withdrawn from the patient. Each of the catheters may be provided with a different shape, size, configuration or implement suited for a specific purpose. For example, angiographic studies typically include the use of at least three cardiac catheters including a right coronary artery catheter, a left coronary artery catheter and a pigtail catheter. Each has a different shape and configuration at its distal end (the end inserted into the patient; the opposite end, is the "proximal" end), each being designed to facilitate placement of the distal end of the catheter at specific locations within the region of the heart. By way of further example, other types of catheters may include balloon dilatation catheters intended to be placed within an obstructed (stenosed) portion of an artery and then inflated under high pressure to expand the lumen of the artery and improve blood flow through the artery. Such a dilatation procedure is commonly referred to as "angioplasty" and has had significantly increased use for nearly two decades in the treatment of coronary artery disease. Still other types of catheters, such as atherectomy catheters, catheters incorporating optical elements for the transmission of light, catheters used in the delivery of a stent, among others, often are used in connection with guidewires.

It is common in the use of wire guided catheters for the physician to withdraw the catheter from the patient and substitute another catheter in its place. When doing so, it is desirable to leave the guidewire in place in order that the guidewire can be used to advance the succeeding catheter directly to the treatment site with a minimum of delay and trauma. In order to maintain the guidewire in place while withdrawing the catheter, the guidewire must be held in its position in the blood vessel as the catheter is withdrawn. The catheter, however, typically is longer than the proximal portion of the guidewire that protrudes out of the patient. Thus, before the catheter is fully withdrawn it completely covers the proximally extending end of the guidewire such that the physician can no longer grasp the guidewire. In order to effectively remove the catheter while permitting the guidewire to remain in place, some means must be provided to prevent the guidewire from being dragged out of position as the catheter is removed. This problem is frequently encountered in coronary angioplasty procedures and, therefore, the present invention, and its background, will be described in the context of a percutaneous transluminal coronary angioplasty (PTCA) system.

Dilatation catheters commonly used in PTCA include an elongate flexible shaft of the order of about 150 cm long having a dilatation balloon mounted to the distal end of the shaft and an inflation lumen extending longitudinally within the shaft from the proximal end to the interior of the balloon so that the balloon may be inflated and deflated. Often such PTCA catheters also are provided with a full length guidewire lumen that receives a guidewire and terminates in openings at the distal tip of the shaft and at the proximal end of the catheter. When the guidewire and catheter are placed within a patient's artery, the guidewire can be manipulated to guide the wire to a desired location. The catheter then can be advanced, guided by the guidewire, to that location.

Typically, the balloon dilatation catheter and guidewire are guided to the entrance to one of the coronary arteries through another previously placed, larger diameter, single lumen catheter (a guide catheter). The guide catheter commonly is percutaneously inserted into the patient's femoral artery and is advanced along the aorta toward the heart. The guide catheter typically is provided with a pre-shaped distal tip adapted to engage and remain at the coronary ostium leading to the coronary artery. Once positioned, the guide catheter remains in place throughout the procedure to provide direct, quick access to the entrance to the coronary artery.

It is common during a PTCA procedure for the physician to exchange the balloon catheter for another catheter. This may occur if the physician initially performed a partial dilatation with a small diameter balloon and then wished to further dilate the patient's artery by using a catheter having a larger balloon. A catheter exchange also may be performed to perform further operations in the artery such as stent placement or other treatment. Such a catheter exchange typically has been accomplished in several ways, all designed to enable withdrawal of the catheter without losing guidewire position.

Among the techniques for effecting a catheter exchange is one in which the conventional guidewire (approximately 175–190 cm long) is removed from the indwelling balloon catheter and is replaced with a longer exchange wire, usually about 300 cm long. The additional length of the exchange wire results in a long proximally protruding portion that is longer than the catheter to be withdrawn. When the balloon catheter is withdrawn, some part of the proximally extending portion of the exchange wire will always be exposed to provide a means by which the exchange wire can be grasped and its position in the blood vessel maintained. After the 300 cm exchange wire has replaced the conventional length guidewire, the original catheter then is withdrawn over the exchange wire, which is grasped and held in place by an assistant. The next succeeding catheter then can be inserted into the patient over the exchange wire. The exchange wire provides a direct path to guide the new catheter to the portion of the blood vessel to be treated. If desired, the exchange wire then may be removed and replaced with a conventional length guidewire, although some physicians may prefer to permit the exchange wire to remain in place for the remainder of the procedure, especially if additional catheter exchanges are contemplated.

The technique of using a long exchange wire is not free from difficulty. The proximally extending end of the exchange wire is quite long and cannot be manipulated easily, should it be desired to do so. Typically, the use of a long exchange wire requires an assistant to hold the proximal end of the catheter at all times so that it does not fall to the floor, become kinked or contaminated. The placement of the exchange wire typically is performed under fluoroscopy to assure that it is properly placed in the patient's blood vessel. The use of an exchange wire also adds to the time and complexity of the procedure.

Another technique omits the necessity for an exchange wire by providing a guidewire extension that is attached to the proximal end of the conventional length indwelling guidewire, thereby effectively extending the length of the portion of the guidewire that protrudes out of the patient. The guidewire length is extended sufficiently to permit the catheter to be withdrawn and a new catheter to be threaded back into the patient without losing guidewire position. U.S. Pat. No. 4,917,103 discloses an illustrative guidewire extension system.

Still another technique for performing a catheter exchange has involved the use of a specially constructed "rapid exchange" catheter having a relatively short guidewire lumen at the distal end of the catheter. The guidewire lumen has a proximal opening located distally of the proximal end of the catheter shaft. In this arrangement, the guidewire passes through the catheter shaft only for a segment of the length of the shaft. The rapid exchange catheter can be moved along the guidewire in "monorail" fashion. Because the guidewire lumen is considerably shorter than the overall length of the catheter, the catheter can be withdrawn from the patient over the original guidewire without dragging the guidewire out of the artery together with the catheter because the length of the guidewire protruding from the patient is longer than the length of the guidewire lumen of the catheter. Thus, a portion of the guidewire is exposed at all times and may be grasped by the physician or an assistant. Among the difficulties presented by the use of a rapid exchange system is that the system does not permit guidewires to be exchanged after the rapid exchange catheter is inserted. For example, if the physician decides that a more flexible guidewire is required, the rapid exchange catheter must be fully withdrawn to access the proximal end of its short guidewire lumen. Moreover, once withdrawn, the catheter cannot direct the new guidewire to the previously achieved position within the coronary artery. The guidewire must be steered anew beyond the distal end of the guide catheter to the treatment site. Another disadvantage in the rapid exchange catheter system is that a rapid exchange catheter cannot be exchanged with a conventional dilatation catheter having a full length guidewire lumen unless an exchange wire or extension wire system is utilized. Additionally, the rapid exchange catheter cannot maintain fluid communication with the region of the blood vessel beyond the distal end of the catheter, should that be desired.

Still other efforts have been made to overcome the disadvantages presented by the use of exchange wires, extension wires and rapid exchange catheters. European patent application Serial No. 90308054.7 filed Jul. 23,1990 discloses an arrangement by which the position of the guidewire is maintained by interposing a balloon within the guide catheter in a manner that, when inflated, the balloon entraps the guidewire in a fixed position relative to the guide catheter. By immobilizing the guidewire with respect to the guide catheter, it is possible to withdraw the indwelling dilatation catheter without requiring the use of extension wires or a rapid exchange catheter. Still other devices have been developed to effectively immobilize the guidewire with respect to the guide catheter, such as a magnetic device described in U.S. Pat. No. 5,269,759 (Hernandez et al.) These devices, in general, tend to be costly, can be awkward to use and require that other compromises be made in order to enable their use.

There has been a need for a simple, effective and inexpensive system and technique for withdrawing an indwelling over-the-wire catheter while leaving the guidewire in place and for a system to facilitate catheter exchanges. It is the general object of the present invention to satisfy that need.

SUMMARY OF THE INVENTION

The invention provides a system and enables a technique in which an over-the-wire catheter can be withdrawn from the patient while maintaining the guidewire in its placed position within the patient. The invention can be practiced with a standard length guidewire, without the use of exchange wires or guidewire extensions and with conventional, non-rapid exchange, over-the-wire catheters. The invention may be practiced with any conventional guidewires. The invention is practiced by the simple expedient of constraining a segment of the proximally protruding portion of the combined guidewire and catheter in a non-linear configuration and then, while so constrained, simply pulling the catheter proximally out of the patient. The catheter shaft is more flexible than the guidewire and can be drawn more readily along the non-linear path. The deformed guidewire, however, is not sufficiently flexible to pass through the non-linear path and, therefore, remains in place. The configuration of the non-linear path required to practice the invention may be varied to accommodate the specific stiffness and frictional characteristics of the particular guidewire and catheter(s). The outer surface of the guidewire and the inner luminal surface of the guidewire lumen of the catheter should have a sufficiently low coefficient of friction and the catheter shaft should have sufficient flexibility relative to the guidewire to enable the catheter to move, in snake-like fashion along the non-linear configuration without binding.

The constraint may be implemented by a holding device that engages a segment of the proximally protruding portion of the catheter shaft that contains the guidewire to retain them in the non-linear configuration. The holding device preferably presents a low friction engagement with the outer surface of the catheter.

The invention has particular utility to effect a catheter exchange. After the indwelling catheter has been removed, another catheter can be threaded onto the proximal end of the guidewire. A segment of the combined guidewire and catheter then can be constrained in the non-linear configuration to enable the catheter to be advanced over the guidewire while maintaining the guidewire in position. The invention may be practiced with conventional guidewires without modification or may be practiced with modified guidewire components in accordance with various aspects of the invention.

It is among the general objects of the invention to provide a new and improved system and method for effecting withdrawal of an indwelling, over-the-wire catheter from a patient while maintaining the position of the guidewire in the patient.

Another object of the invention is to provide a new and improved system and technique for effecting exchange between an indwelling over-the-wire catheter and another catheter.

A further object of the invention is to provide a system and technique of the type described that can be used with a conventional guidewire.

Another object of the invention is to provide a system and technique for effecting a catheter exchange that does not require the use of exchange wires or extension wires.

A further object of the invention is to provide a system and technique for withdrawing a catheter and for effecting a catheter exchange that can be practiced with a conventional guidewire and without using a rapid exchange catheter.

Still another object of the invention is to provide devices and techniques for effecting a catheter withdrawal or a catheter exchange in which the position of the guidewire can be maintained without modification to the guide catheter and without using a device for securing the position of the guidewire directly with respect to the guide catheter.

An additional object of the invention is to provide a system and procedure for withdrawing a catheter and for effecting a catheter exchange while maintaining position of the guidewire in which the catheter and the guidewire are together constrained externally of the patient and in a manner that maintains the guidewire in position while enabling the catheter to be withdrawn and replaced.

A further object of the invention is to provide a system that enables a rapid exchange catheter to be exchanged with an over-the-wire catheter having a full length guidewire lumen, with the exchange being performed over a conventional length indwelling guidewire.

Another object of the invention is to provide devices and techniques of the type described that are inexpensive and simple to make and use.

DESCRIPTION OF THE DRAWINGS

The foregoing and other objects and advantages of the invention will be appreciated more fully from the following further description thereof, with reference to the accompanying drawings wherein.

DESCRIPTION OF THE ILLUSTRATIVE EMBODIMENTS

Figure 1:
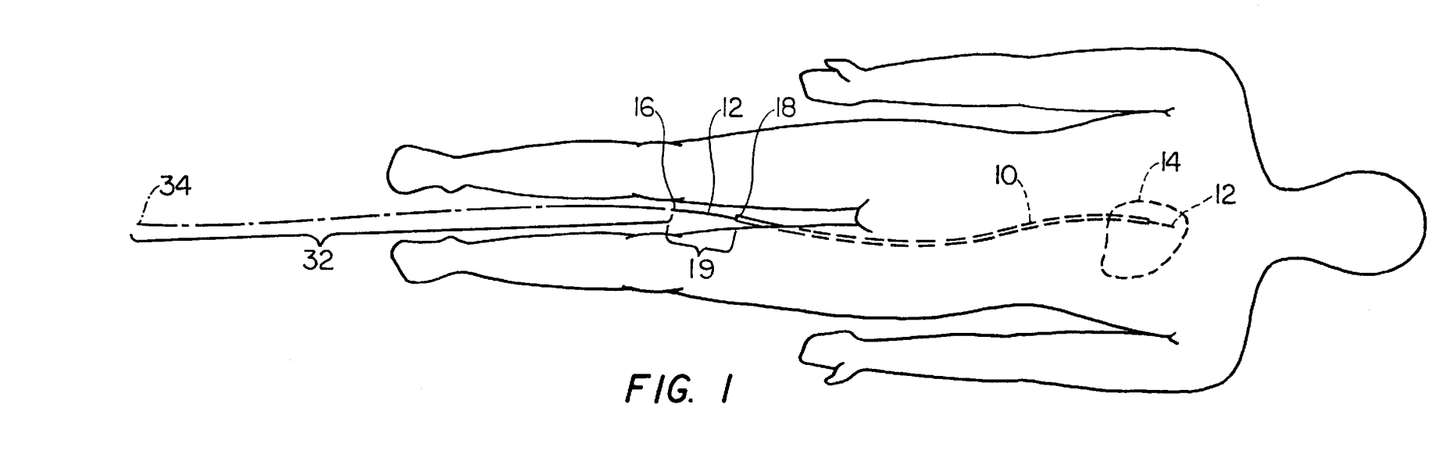
FIG. 1 is a diagrammatic illustration of a patient undergoing coronary catheterization.

FIG. 1 illustrates, in highly diagrammatic form, a catheter 10 and guidewire 12 which have been inserted into a patient's femoral artery and have been advanced to the region of the patient's heart where a desired procedure will be performed. The guidewire 12 and catheter 10 will have been inserted and placed in the artery in accordance with well known procedures typically including the preliminary placement of a single lumen guide catheter (not shown in FIG. 1).

When it is desired to exchange the indwelling catheter 10 for another, it is important that the guidewire 12 be maintained in its position within the patient's artery so that it may guide the next succeeding catheter quickly and efficiently to the intended site in the patient's vascular system. Typically, the clearances between the guidewire 12 and inner lumen of the catheter 10, coupled with the bends which the catheter and guidewire must follow along the patient's vascular system, are such that withdrawal of the catheter 10 tends to drag the guidewire out with the catheter 10. In order to maintain the guidewire in place while the catheter 10 is withdrawn, it is necessary to hold the guidewire 12 by its proximal end 16 while withdrawing the catheter 10 over the guidewire 12. That has presented some difficulty because the proximal extremity 16 of a conventional guidewire only protrudes beyond the proximal end 18 of the catheter by an amount that is substantially less than the length of the catheter 10. Therefore, it has been necessary to resort to use of the systems and techniques discussed above in order to perform a catheter exchange.

Figure 2:
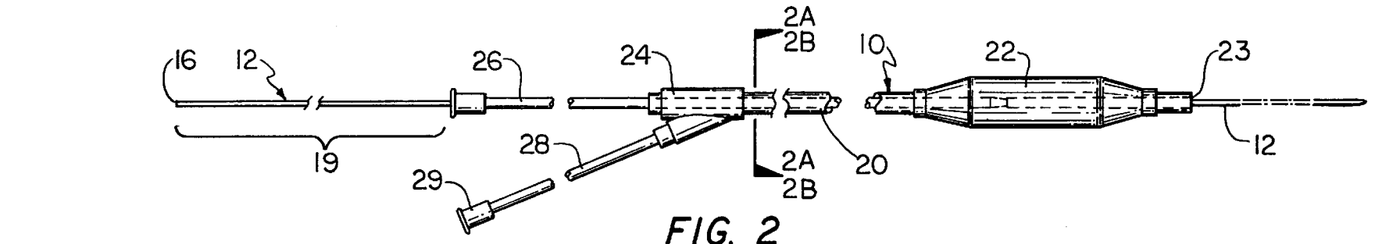
FIG. 2 is a somewhat diagrammatic, fragmented illustration of a conventional over-the-wire catheter and guidewire.
Figure 2A:
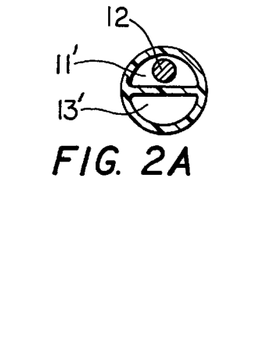
FIG. 2A is a cross-sectional illustration of a two-lumen extruded type of catheter shaft as seen along the line 2A—2A of FIG. 2.
Figure 2B:
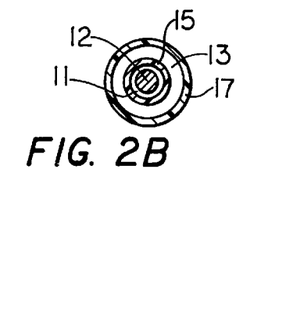
FIG. 2B is a sectional illustration of a two-lumen, two-tube coaxial type of catheter shaft as seen along the line 2B—2B of FIG. 2.

FIG. 2 illustrates the proximal (at the left) and distal (at the right) ends of a conventional over-the-wire catheter with the ends of the guidewire protruding out of the corresponding ends of the catheter 10. The illustrated catheter 10 includes an elongate, flexible shaft 20, formed with two lumens 11', 13' (FIG. 2A) or 11, 13 (FIG. 2B) extending through the shaft, one of the lumens 11 or 11' extending fully through the length of the shaft to receive a guidewire 12 and the other 13 or 13' to communicate between the proximal end of the catheter and a dilatation balloon 22 mounted at the distal end of the catheter. The distal end of the guidewire lumen 11 or 11' terminates in an outlet orifice 23 through which the distal end of the guidewire 12 protrudes. The inflation lumen 13 or 13' terminates within the balloon 22 and serves to communicate inflation medium (typically a radiopaque liquid) to and from the balloon 22 to effect inflation or deflation. The catheter shaft 10 may be formed from a variety of conventional polymers used to form catheter shafts, polyethylene and nylon being among the more common materials. The catheter shaft 20 may be of any conventional construction such as, for example, an extruded two lumen shaft (FIG. 2A) or a pair of coaxial tubes 15, 7 (FIG. 2B) in which the inner tube defines the guidewire lumen 11. The material from which the catheter shaft is formed and which defines the guidewire lumen, should have sufficiently low frictional characteristics so as to cooperate with the guidewire to enable the catheter shaft to easily slide over the guidewire in the practice of the invention. The outer surface of the guidewire 12 may be coated with a material to enhance its lubricity, such as Teflon, hydrophilic or other materials commonly used for such purpose.

The proximal end of the catheter includes a bifurcate fitting 24 which joins a guidewire leg 26 and an inflation leg 28 to the catheter shaft 20 to communicate, respectively, with the guidewire and inflation lumens 11, 13. The inflation leg 28 has a fitting 29 at its proximal end that may be connected to a source of pressurized inflation medium. A similar connector fitting may be attached to the proximal end of the guidewire leg 26.

The operation and function of a conventional over-the-wire catheter and guidewire is well known to those familiar with the art. Should it be desired to effect a catheter exchange, one common approach is to use an extension wire that can be attached to the proximal end of the guidewire so that the total overall length of the guidewire and extension wire (not shown) may be of the order of 300 cm long. The additional effective length, as compared to the conventional guidewire length is represented by the phantom line 32 in FIG. 1. The length of the extended guidewire is such that its free proximal end 34 is spaced from the proximal end of the guide catheter by a distance that is greater than the length of the operating (dilatation) catheter. Consequently, a portion of the guidewire or extension always is exposed and can be grasped by the physician to maintain the position of the guidewire as the catheter exchange is performed. Such a guidewire extension system is disclosed, for example, in U.S. Pat. No. 4,917,103 issued Apr. 17, 1990.

Figure 3:
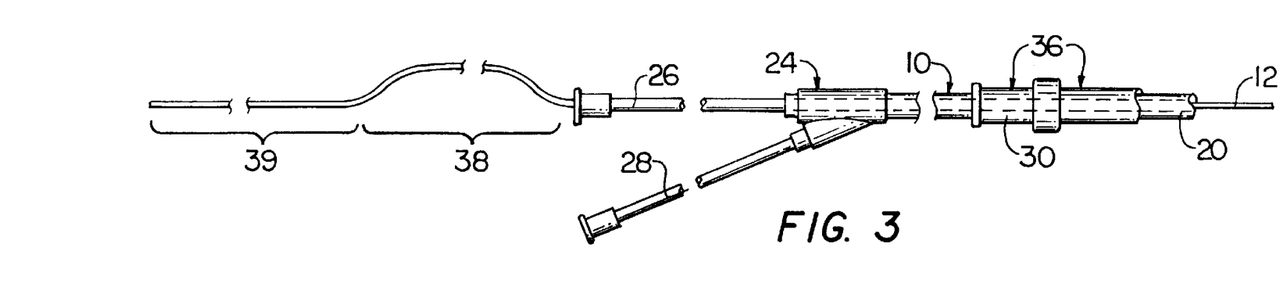
FIG. 3 is a diagrammatic, fragmented illustration of the proximal ends of the guide catheter, the operating catheter and a guidewire in accordance with one illustrative embodiment of the invention.

FIG. 3 illustrates the proximal ends of each of the guide catheter 36, the dilatation catheter 10 that is received within the guide catheter 36, and the guidewire 12 that is received within the guidewire lumen of the dilatation catheter 10. In accordance with one embodiment of the invention, the proximal portion of the guidewire 12 may be provided with a segment that is deformed to a non-linear configuration. In the illustrative example of FIG. 3, the non-linear configuration may take the form of a curved segment 38 as compared to the otherwise linear (generally straight) configuration of the proximal end of the guidewire illustrated in FIG. 2. Although in the immediately following description, the curved segment 38 will be described as having been deformed inelastically, it should be understood that the invention also may be practiced with guidewires in which a proximal segment of the guidewire is deformed elastically to its non-linear configuration.

The guidewire may be constructed in any of a number of configurations well known in the art. For example, for a guidewire intended for use in percutaneously transluminal coronary angioplasty, it may be desirable to embody a steerable guidewire construction such as that disclosed in U.S. Pat. No. 4,545,390 (Leary). Such steerable guidewire is characterized by an elongate flexible shaft, typically formed from metal, such as stainless steel, that is longitudinally flexible yet displays a degree of torsional rigidity that enables rotation applied to the proximal end of the guidewire to be transmitted controllably to the distal end of a guidewire that protrudes distally beyond the distal end of the catheter. Although the guidewire is longitudinally flexible, it nevertheless is stiffer than the catheter with which it is used. Guidewires used in coronary angioplasty commonly have a shaft of a diameter of between about 0.012 to about 0.018 inches diameter, with 0.014 inch diameter being most commonly used. The non-linear segment 38 should be formed far enough from the free proximal extremity of the guidewire to leave a proximal tail 39 sufficiently long so that the proximal extremity of the guidewire will be exposed proximally of the guidewire leg 26 when the non-linear segment 38 is disposed distally of the bifurcate fitting 24 and within the catheter shaft 20. By way of example, for use with nearly all commercially available coronary angioplasty catheters, a proximal tail segment of the order of twenty-five centimeters long should be sufficient to enable placement of the non-linear segment within the catheter shaft 20, while still maintaining an exposed end of the guidewire. Other guidewire constructions, of course, may be employed, as long as a proximal segment of the guidewire is capable of defining and assuming a non-linear configuration. As described in further detail below, that may be accomplished by deforming the proximal end of the guidewire itself either elastically or inelastically or by attaching a non-linear segment to the proximal end of a guidewire.

Figure 4:
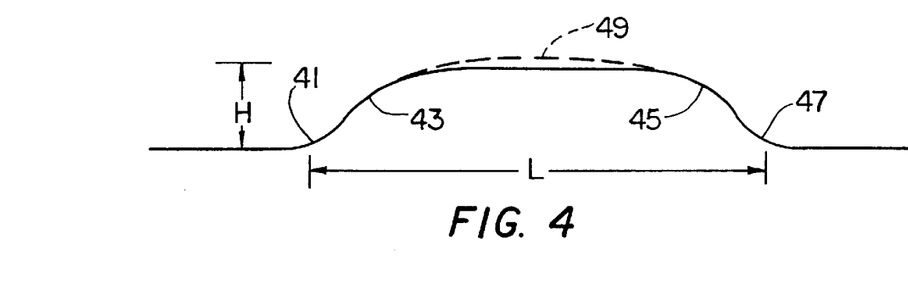
FIG. 4 is a enlarged diagram of the non-linear shape at the proximal end of the guidewire shown in FIG. 3.

FIG. 4 is an illustration of one embodiment of a non-linear segment formed permanently (i.e., inelastically) in the proximal region of the guidewire. The shape of the non-linear segment 38 shown in FIG. 4 includes a transversely displaced portion extending over a length L of about 8 centimeters and having a height H, that is, displaced from the longitudinal axis of the guidewire, of about 1.5 centimeters. Although the length L and height H may be varied, preferably the ratio of the length L to the height H should be no more than about ten. The non-linear segment 38 may define three or more bends as shown in FIG. 4 which shows, in solid line, an arrangement in which there are four such bends indicated at 41, 43, 45 and 47. The segment between bends 43 and 45 may be substantially straight or may itself be curved, as indicated in phantom at 49, in which case the non-linear segment would have three curves (see also FIG. 16). When the non-linear shape includes a plurality of bends, at least two adjacent bends should be provided with a reverse curvature, as the successive bends 41, 43. It should be understood, however, that non-linear shapes other than those illustrated in FIGS. 4 and 16, but with modified dimensions and geometries, may be employed, depending on the frictional and stiffness characteristics of the catheter and guidewire. It may be noted that, depending on the frictional and stiffness characteristics of the particular catheter and guidewire in use, the invention may be practiced by providing only a single permanent bend adjacent the proximal region of the guidewire. It may be desirable, when employing a single permanent bend, to restrain that non-linear segment in a configuration in which one or more portions of the guidewire adjacent the permanent bend is (are) restrained in a non-linear curve or bend which is not permanent (i.e., which is elastically deformed).

The guidewire may initially have a linear proximal end (as in FIG. 2) but, when it is desired to perform a catheter exchange, a segment of the proximally protruding portion of the guidewire then is provided with the desired non-linear configuration illustrated in FIG. 3. The non-linear configuration may be formed, by deforming the guidewire and is permanent in the sense that the deformed portion of the guidewire will remain in the non-linear shape in the absence of external stress. The non-linear configuration should be selected so that it can be disposed within a holding device that defines a path through which the non-linear guidewire shape cannot be readily drawn. That path may be non-linear and may correspond to the shape of the nonlinear portion of the guidewire. As will be described, the relative flexibility of the catheter shaft and the guidewire are such that the catheter shaft can be drawn through the path defined by the holding device while the guidewire cannot. Thus, the cooperation between the holding device, the non-linear guidewire segment and the flexible catheter shaft enable the catheter to be pulled through the holding device while the holding device maintains the guidewire in position.

Figures 11, 12, 13:
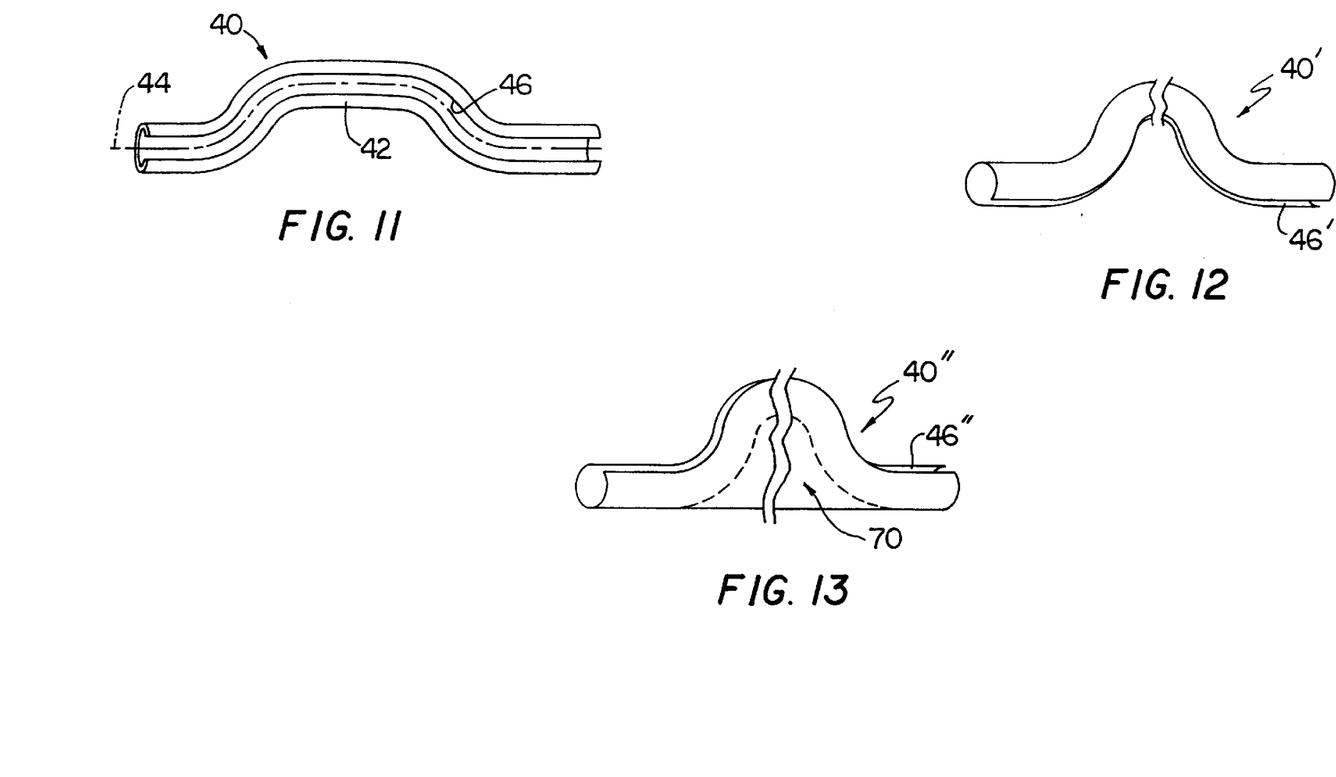
FIGS. 11–13 are illustrations of one general type of holding device.
Figure 22:
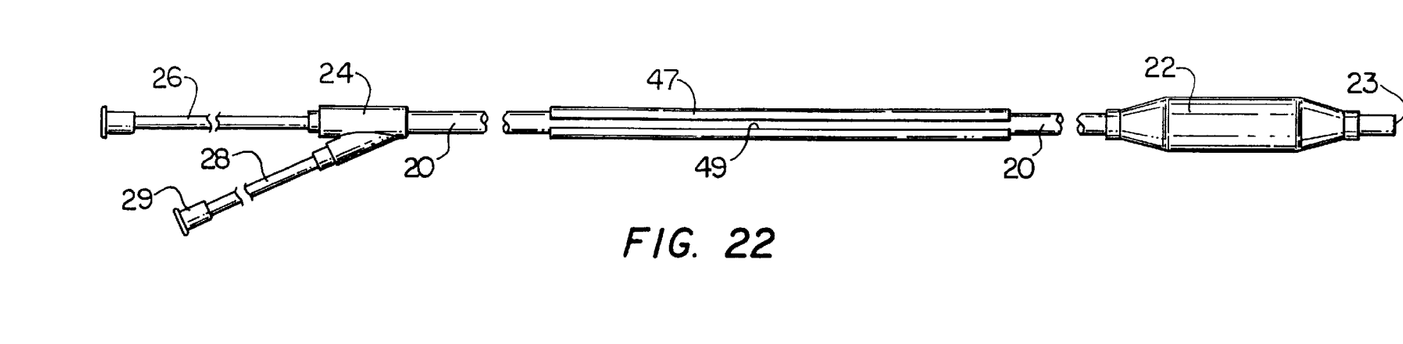
FIG. 22 is an illustration of a portion of a catheter shaft to which a flexible sleeve has been attached with the flexible sleeve having a lubricious inner surface.

FIG. 11 illustrates, diagrammatically, one type of holding device 40 that may include a body 42 formed to define a pathway, shown in phantom at 44, having a configuration through which the non-linear portion 38 of the guidewire cannot readily pass but through which the more flexible catheter shaft 10 can pass easily. The holding device may, as illustrated, be formed in a tubular configuration and preferably is sufficiently rigid to hold its shape as the catheter is drawn therethrough. The holding device includes a means to enable the device to be placed about the catheter shaft 20. In the embodiment illustrated in FIG. 11, that means may take the form of a simple side slot 46 that provides transverse access to the internal pathway 44. The holding device 40 may be formed from a suitably rigid plastic and should be constructed so that it will permit the flexible catheter shaft to be drawn through the holding device 40 while presenting resistance to longitudinal movement of the less flexible guidewire 12 relative to the holding device. In order to facilitate such relative movement, it is desirable that the inner surface of the guidewire lumen in the catheter shaft and the outer surface of the guidewire are such that there is the requisite degree of lubricity between the two and suitable coatings may be applied to enhance a low coefficient of friction. Similarly, the drag presented by the holding device to catheter advancement should be maintained as low as possible and where the drag would be presented in the form of sliding friction, as when the holding device of FIG. 11 is used, it may be desirable to suitably coat the inner surface of the holding device. In a further modification, the catheter itself may be provided with a flexible tubular sleeve 47 (FIG. 22) that has a lubricious inner surface to enable the catheter shaft 20 to slide easily through the sleeve, even when the sleeve 47 is in a non-linear configuration. This embodiment may be used when the catheter shaft and included guidewire are held and constrained in the non-linear configuration by means that present more frictional drag on the catheter than would be desired. The sleeve may be formed simply from a tubular section of polyethylene (or other material having good lubricity with the outer surface of the catheter). The sleeve may be provided with a longitudinal side slit 49 to facilitate attachment to the catheter shaft.

Figure 5:
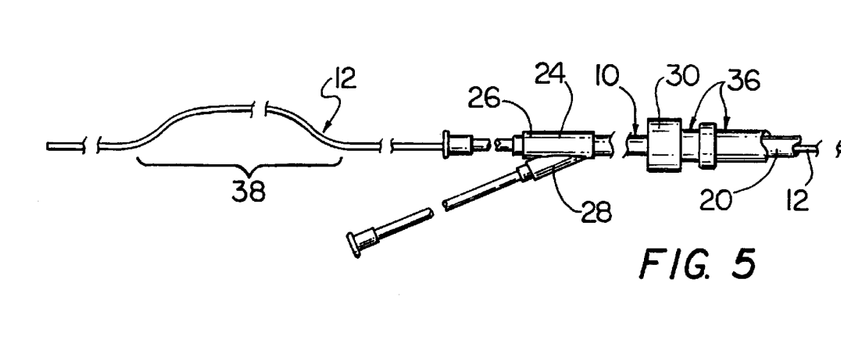
FIG. 5 is a fragmented, diagrammatic illustration of the proximal ends of the assembly of the guide catheter, an operating catheter in the form of a balloon dilatation catheter and a guidewire, and of the distal end of the balloon catheter and guidewire, with the balloon having been inflated to partially dilate a stenosis in the blood vessel.
Figure 6:
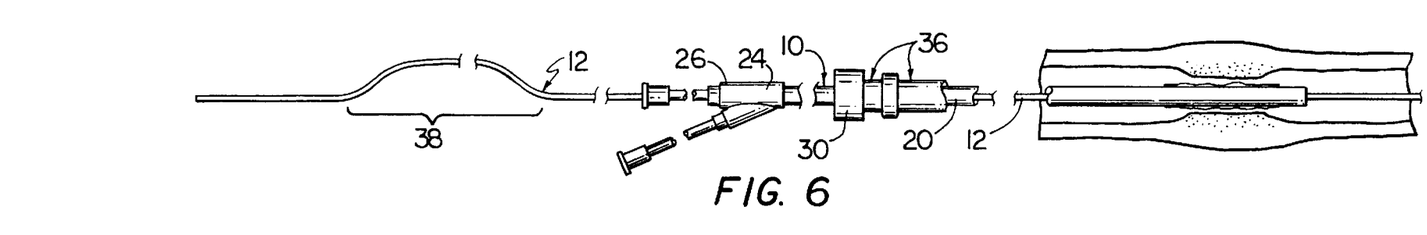
FIG. 6 is an illustration of the arrangement shown in FIG. 5 with the stenosis having been partly dilated and with the balloon deflated.

FIGS. 5–10 illustrate, sequentially and diagrammatically, the manner in which the invention may be used in practice. FIG. 5 illustrates a balloon dilatation catheter 10 and guidewire 12 that have been advanced through a guide catheter 36 (for ease of illustration only the proximal end of the guide catheter is shown) and further illustrates the balloon 22 in an expanded configuration in which it has dilated a stenosis S within an artery A. The guidewire 12 will have been preliminarily advanced through the undilated stenosis S and then the catheter 10 will have been advanced over the guidewire to place the balloon 22 within the stenosis in readiness for balloon inflation. The region of the dilated stenosis in FIG. 5 illustrates a condition in which a physician may elect to perform a catheter exchange because the balloon 22, when inflated to its maximum diameter or for other reasons, was unable to dilate the stenosis S as fully as may have been desired. For example, it may have been intended to dilate the stenosis S to a diameter equal to or slightly greater than the native inner diameter 23 of the artery A.

In order to effect a catheter exchange in accordance with one aspect of the present invention, a segment of the proximally protruding linear, undeformed end of the guidewire is inelastically deformed to a desired non-linear configuration. The non-linear segment 38 may be formed by directly deforming the proximal region of the guidewire 12. As described further below, a tool may be provided to effect the deformation. Alternately, in some cases, it may be preferable to begin the procedure with a guidewire having a pre-formed non-linear segment 38. In yet another embodiment, the invention may be practiced by attaching a short non-linear segment to the proximal end of the guidewire.

Figure 7:
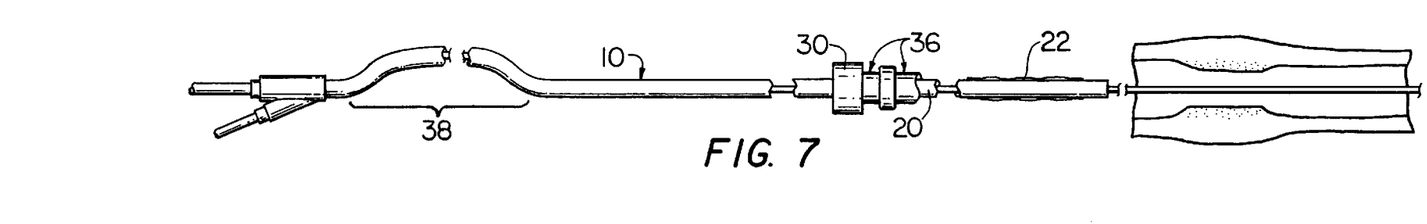
FIG. 7 is an illustration of the apparatus of FIG. 6 with the dilatation catheter having been pulled back with a proximal portion of the catheter shaft overlying the non-linear portion of the guidewire.
Figure 8:
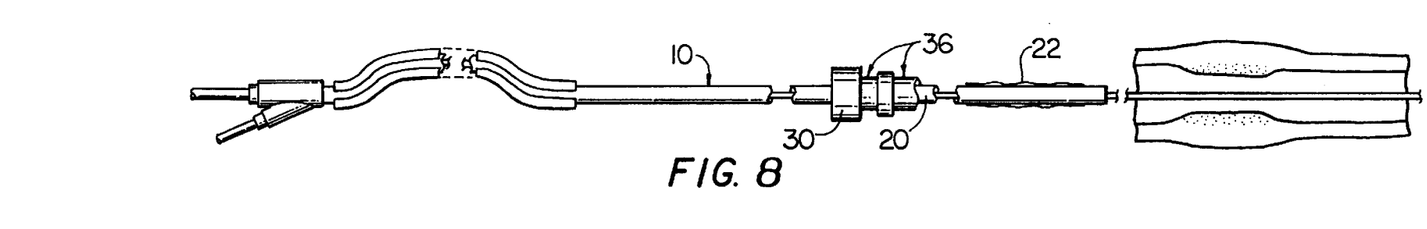
FIG. 8 is an illustration similar to FIG. 7 with one embodiment of a holding device attached to a proximal portion of the guidewire-containing catheter in the region of non-linearity.

With the proximal region of the guidewire having been deformed to define the non-linear segment and with the balloon of the catheter having been deflated (FIG. 6), the catheter exchange may be effected by first withdrawing the catheter 10 from the guide catheter 36 while grasping the exposed portion of the guidewire 12 to maintain the guidewire in position. The catheter is withdrawn so that the bifurcate fitting 24 passes over the non-linear portion until the non-linear portion of the guidewire is disposed within a flexible portion of the catheter shaft 20. As described above, the catheter shaft is substantially more flexible than the guidewire. The relative flexibilities are such that the catheter shaft can be drawn easily over and along the permanently formed non-linear portion 38, in snake-like fashion, so that that portion of the catheter shaft 20 assumes the non-linear configuration (FIG. 7). As shown in FIG. 8, a holding device, such as the device 40 illustrated in FIG. 11 then is attached to the non-linear region of the catheter shaft and guidewire.

It may be noted that as the catheter shaft is withdrawn proximally, the deflated balloon is drawn proximally out of the stenosis toward, and possibly into, the guide catheter. With the physician holding the holding device in place, the catheter then can be withdrawn further proximally to withdraw the catheter entirely out of the guide catheter 36 and the Tuohy-Borst adapter 30 on the proximal end of the guide catheter 36. The withdrawal of the catheter will not drag the guidewire along with the catheter because the path through the holding device does not permit passage of the non-linear segment of the guidewire. Thus, the balloon catheter may be withdrawn to the position illustrated in FIG. 9 in which the distal end of the catheter has been withdrawn out of the Tuohy-Borst adapter 30 and where a segment 52 of the guidewire 12 may be reexposed. The adapter 30 then can be tightened down securely about the guidewire to lock the guidewire in place relative to the guide catheter and also to reduce interim leakage of blood from the guide catheter. Alternately, the physician may simply grip the exposed segment 52. With the guidewire so held, the holding device 40 can be removed and the catheter can be fully withdrawn and separated from the guidewire.

Figure 9:
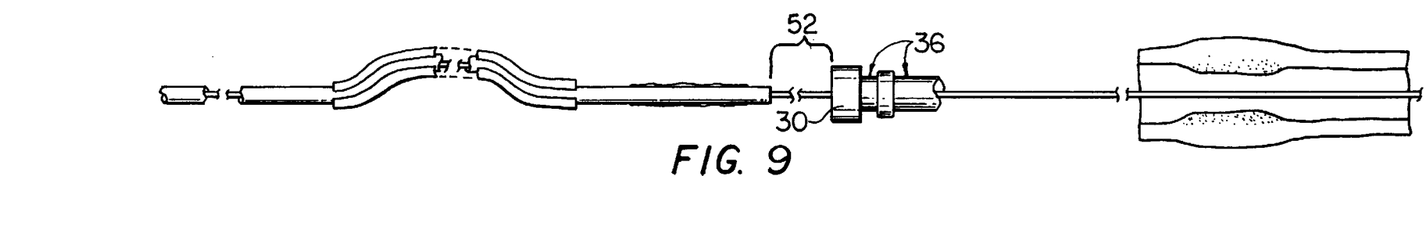
FIG. 9 is an illustration of the apparatus of FIG. 5 with the operating catheter having been drawn proximally over the guidewire and with the distal end of the operating catheter withdrawn from the Tuohy-Borst adapter at the proximal end of the guide catheter.
Figure 10:
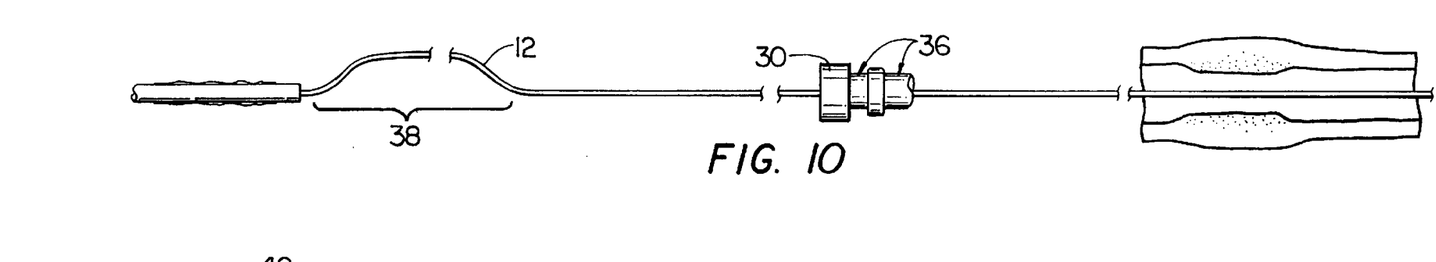
FIG. 10 is an illustration of the proximal end of a new catheter having been threaded onto and partly advanced along the proximal end of the guidewire.

After the indwelling catheter has been completely removed, another catheter (e.g., a catheter having a balloon inflatable to a larger diameter than the original catheter or one carrying a stent) is threaded onto the free proximal end of the guidewire (FIG. 10) and is advanced along the guidewire toward the Tuohy-Borst adapter 30. The Tuohy-Borst adapter 30 (or the physician) will sufficiently grip the guidewire during that catheter advancement to prevent guidewire movement. At some point during the advancement of the catheter over the guidewire, and after the flexible shaft 20 of the catheter has advanced along and onto the non-linear portion 38 of the guidewire 12, the holding device 40 then is reattached as illustrated in FIG. 9. With the holding device 40 reattached, the grip on the guidewire can be released. The physician then can hold the holding device 40 in place while continuing advancement of the balloon catheter into the guide catheter 36. After the balloon catheter has been advanced sufficiently so that the proximal end of the guidewire 12 is exposed proximally of the guidewire leg 26, the holding device 40 can be detached. The balloon catheter then can be advanced while the proximally protruding end of the guidewire is manually held to maintain guidewire position in the artery.

From the foregoing, it will be appreciated that an over-the-wire catheter can be exchanged for another over-the-wire catheter without the use of exchange wires, extension wires, rapid-exchange catheters or other relatively complex special devices for maintaining guidewire position during balloon catheter withdrawal or exchange.

Other configurations for the holding device may be employed. FIG. 12 illustrates a modified device 40' similar to that shown in FIG. 11 except that the slot 46' is disposed at the underside of the device rather than along the side. FIG. 13 illustrates yet another configuration 40' of the device having a general contour similar to that of FIGS. 11 and 12 but in which the slot 46' is formed along the top surface of the device and in which a web 70 is provided beneath the arched portion to rigidify and to facilitate holding the device.

Figure 14:
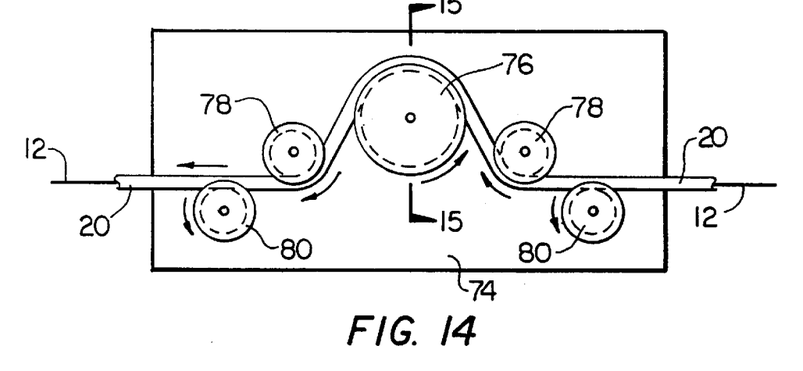
FIG. 14 is an illustration of another type of holding device.
Figure 15:
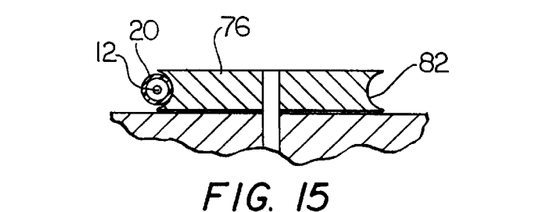
FIG. 15 is a sectional illustration of one of the rollers embodied in the device of FIG. 14 as seen along the line 15—15 of FIG. 14.

In another embodiment of the holding device, the path through the holding device can be defined by an arrangement of rollers adapted to provide low drag on the outside of the catheter. FIG. 14 shows one such arrangement that includes a frame 74 to which a plurality of guide rollers are rotatably mounted and which cooperate to define the non-linear path. At least three such rollers are provided, including a main roller 76 and a pair of secondary rollers 78. Preferably an additional pair of end rollers 80 are provided. The rollers are spaced and oriented to prevent movement of the non-linear portion of the guidewire 12 while permitting advancement of the flexible catheter shaft 20. The arrows on the rollers in the drawing indicate their direction of rotation when the catheter is advanced through the device. Each of the rollers 76, 78, 80 preferably has a grooved periphery 82 that is receptive to the catheter to retard inadvertent disengagement of the catheter and guidewire from the fixture. The portion of the catheter shaft 20 that contains the non-linear portion of the guidewire 12 can be placed easily in the device with the catheter and guidewire being threaded through the rollers as shown. The catheter then can be advanced, as suggested by the arrows, with the guidewire being enabled to pass through the non-linear path and being retained in place.

Figure 16:
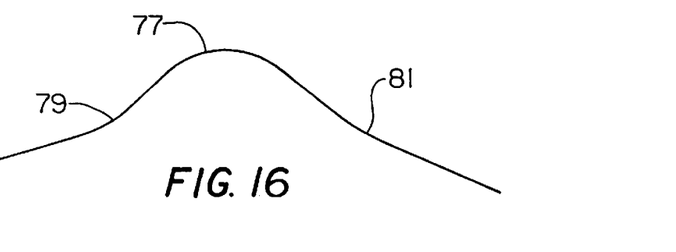
FIG. 16 is an illustration of the shape that was assumed by a permanently deformable guidewire that was placed in the fixture of FIG. 14, illustrating the nature and extent of the shape of the deformation and the shape to which the guidewire returned after removal from the holding device.

The arrangement of rollers 76, 78, 80 may itself serve as a device to deform a portion of the guidewire into a non-linear configuration. To that end, the rollers may be selected to have diameters and may be mounted on rotational axes positioned and arranged so that when a linear portion of the catheter containing the guidewire is wrapped about and through the path defined by the rollers, the bends defined by the path will define a sufficiently short radii to effect permanent deformation of the guidewire to a non-linear configuration. FIG. 16 illustrates the actual permanent bend to which a guidewire segment was deformed when wrapped about the rollers of the device as shown in FIG. 14. That deformed configuration may be considered to include a main curve 77 defined by the relatively large diameter guide roller 76 and a pair of smaller radius secondary curves 79, 81 defined by the guide rollers 78, 80. It will be appreciated that often when the catheter and guidewire have been threaded through the device, although the guidewire will have been permanently deformed, it will retain some residual elasticity so that when it is later withdrawn from the fixture, the deformed portion may spring partially back as illustrated in FIG. 16. Thus, a catheter containing a guidewire may simply be threaded through a fixture having a non-linear path defined at least in part by one or more rollers (or equivalent path-defining elements) that also may be spaced and arranged to effect the permanent deformation of the guidewire to a functional non-linear shape. The catheter and guidewire need only be placed in the fixture, thereby simultaneously deforming and retaining the guidewire. The catheter then can be removed over the free proximal end of the guidewire with the guidewire being retained in place.

Figure 17:
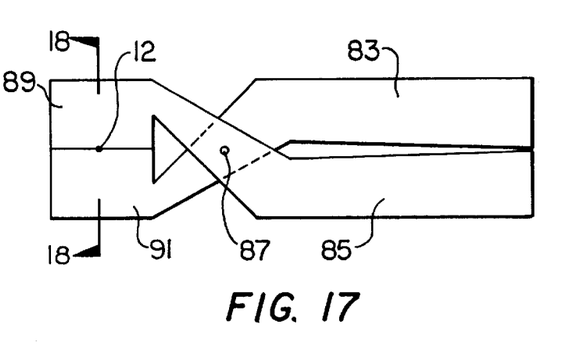
FIGS. 17 and 18 are illustrations of a scissors-like device for permanently deforming a wire into a non-linear shape in accordance with one aspect of the invention.
Figure 18:
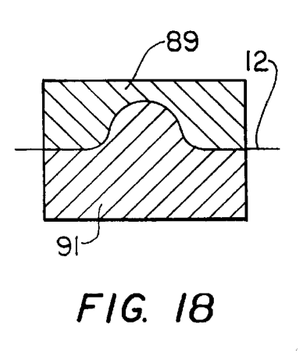

The permanently deformed non-linear segment 38 may be formed by other means. The configuration illustrated generally in FIG. 3 may be formed by a wire shaping tool such as that shown diagrammatically in FIGS. 17 and 18. The shaping tool may be in the form of a scissors-like arrangement having a pair of handles 83, 85 connected at a pivot 87 that open and close a pair of jaws. One of the jaws includes a female die 89 and the other includes a mating male die 91, the dies being shaped as suggested diagrammatically in FIG. 18 to deform the wire into the desired shape.

Figure 19:
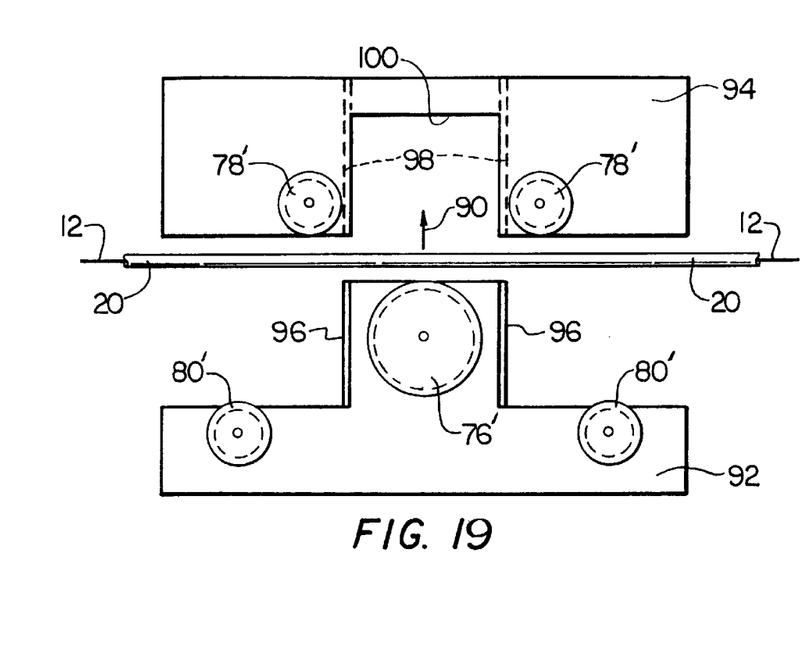
FIG. 19 is a plan illustration of a modified embodiment of a holding device shown in FIG. 14, modified so that the rollers are mounted on separate base sections that are slidable together to enable the device to also shape the guidewire and catheter.

FIG. 19 illustrates another embodiment of a holding fixture having an arrangement of guide rollers similar to that shown in FIG. 14 but in which the base is formed as two slidably connectible sections 92, 94 that carry the guide rollers so that they can be separated to allow insertion of a portion of a catheter and included guidewire. The sections 92, 94 then can be closed together as suggested by the arrow 90, to cause the rollers to engage and bend the catheter 20 and guidewire 12 sufficiently to deform the guidewire to the non-linear configuration and then to retain the guidewire in that configuration as the catheter is withdrawn. To that end, each of the slidably mateable sections 92, 94 carries some of the guide rollers of the array. The sections may be slidably connected for movement toward and away from each other by tongues 96 formed on one section 92 and receptive grooves 98 formed on the other section 94. The section 92 may be provided, for example, with three rollers, including a main guide roller 76' and a pair of laterally spaced outer rollers 80'. The other section 94 may include a pair of laterally spaced secondary rollers 78'. The other section 94 has a cut-out portion 100 to enable the main guide roller 76' and the minor guide rollers 80' to be advanced transversely beyond the secondary rollers 78' to a configuration as shown in FIG. 14. The rollers and frame sections are arranged so that when the frame sections are brought together, the array of rollers will cooperate to define the desired non-linear path. Thus, a section of a catheter shaft with the guidewire extending therethrough can be located along and between the two sections. As the sections are brought together, the catheter and included guidewire is engaged progressively by the guide rollers and when the parts have been brought fully together, they may simply be held together by the physician while the catheter is withdrawn. It should be understood that the foregoing is for illustration only and although the device is described as using an array of five guide rollers, in some instances, fixed guide pins or other functionally equivalent path-defining members may be used instead of rollers.

Guidewires most commonly are formed from stainless steel which has proved to provide an excellent compromise of the various characteristics desirable in a guidewire. Stainless steel wire is biocompatible, flexible, yet can be constructed in a guidewire that displays a high degree of torsional rigidity so that the distal end of the guidewire can be controllably steered from the exposed proximal end of the guidewire. Although the present invention can be practiced with a conventional guidewire having a stainless steel shaft, it may be desirable, in some instances to provide a more secure grip on the non-linear portion of the guidewire that can be achieved, in a permanently deformable material by using a material having a higher modulus of elasticity than stainless steel. To that end, the guidewire may be formed to include a proximal section formed from wire having a higher modulus of elasticity, such as from tungsten or a tungsten alloy wire which has a modulus of elasticity of the order of 45,000,000 p.s.i. as compared to about 29,000,000 p.s.i. for stainless steel. Although having a higher modulus of elasticity, the non-linear shape to which it will be deformed will present sufficient strain to effect a permanent distortion in the tungsten wire. Having been formed from a material with a higher modulus of elasticity, the non-linear segment will be stiffer, will have greater resistance to further deformation and will present greater resistance to being pulled out from the holding device as the catheter is withdrawn. The use of a higher modulus material for the proximal end of the guidewire enables the catheter to be stripped through the holding device at a faster rate than with a less stiff non-linear portion as stainless steel. In this embodiment of the invention, the proximal portion of the guidewire may be formed from a tungsten segment having the same diameter as the rest of the guidewire. The high modulus segment should be longer than the distance between the catheter bifurcate 24 and the proximal end of the guidewire tubular segment 26. It should be longer than that by an amount slightly greater than the length of the non-linear segment 38 in order to assure that the proximal end of the guidewire will be exposed at the proximal end of a catheter until the non-linear segment is disposed within a sufficiently flexible portion of the catheter shaft. A length of about twenty-five to thirty-five centimeters should be enough to accommodate most commercially available catheters.

Figure 20:
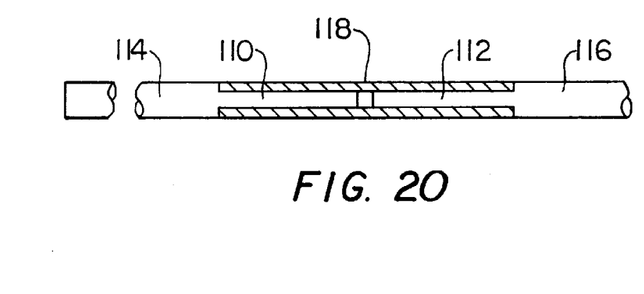
FIG. 20 is an illustration of the connection between a guidewire that has been modified to include a proximal segment having a different modulus of elasticity than the more distal segment.

FIG. 20 illustrates a connection between the distal end of a proximal guidewire segment having a modulus different than the modulus of the proximal end of the guidewire. The ends 110, 112 of the different modulus wires 114, 116 may be reduced to fit within the opposite ends of a length of hypotubing 118. The parts may be secured together by a suitable adhesive, such as a cyanoacrylate adhesive. The connection may be used with a proximal guidewire segment having a greater modulus of elasticity than the more distal portions of the guidewire (as in the example described above) or to attach a proximal guidewire segment having a lesser modulus than the more distal sections, such as by the use of a lower modulus superelastic alloy.

Figure 21:
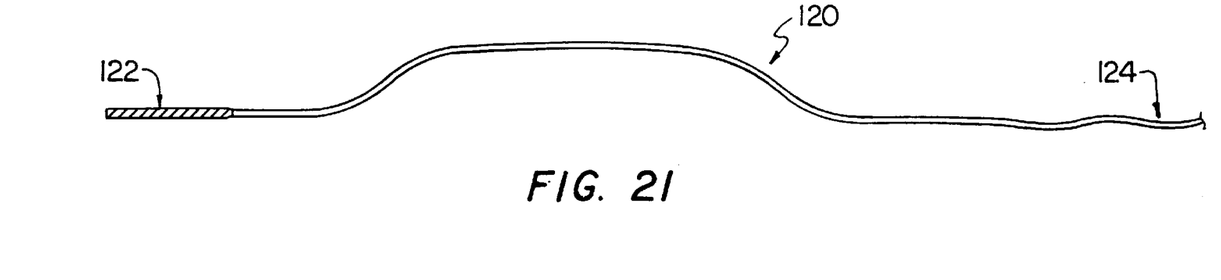
FIG. 21 is an illustration of an attachment wire embodying the invention that may be attached to a commercially available standard length guidewire.

In some instances, it may be desirable to practice the invention while maintaining the proximal end of the wire in its original linear configuration, that is, without deforming the guidewire. That mode of operation may be achieved by providing a relatively short (e.g., 25 to 35 cm) attachment wire at the proximal end of the guidewire in which the non-linear segment has been or can be formed. One such device is illustrated in FIG. 21 which illustrates the attachment wire 120 having a connector element 122 (124) at one or both of its ends. The connectors 122 (124) are selected to be connectible to the proximal end of a compatible commercially available guidewire having a mating connector element used to connect guidewire extensions. Illustrations of such guidewire-to-extension wire connection may be found in U.S. Pat. Nos. 4,827,941 (Taylor et al.), 5,113,872 (Jahrmarkt et al.) and 5,133,364 (Palermo et al.), the disclosures of which are hereby incorporated by reference herein, in their entireties. In the illustration, connector element 122 is meant to suggest the Palermo device and 124 the Taylor device. The attachable segment preferably is formed from a high modulus material such as a tungsten alloy.

It also should be appreciated that even with a permanently deformed nonlinear segment formed in the guidewire, the guidewire, if embodying a steerable construction (such as disclosed in U.S. Pat. No. 4,545,390) will still maintain its steerability. The guidewire may be steered from a location distal of the non-linear segment or from a portion of the non-linear segment itself, or even from a location along the proximal tail. Guidewire torquing devices, connectible to the guidewire well known in the art, may be used to facilitate steering.

From the foregoing, it will be appreciated that the invention provides a simple and easy to use technique and apparatus for removing an over-the-wire catheter from a patient while maintaining the position of the guidewire. The invention achieves this objective without the use of exchange wires, long extension wires, rapid-exchange catheters or other supplemental connectors between the guide catheter and the guidewire. The invention may be practiced with presently available standard length guidewires.

As mentioned above, the invention may be practiced by providing a permanently deformed non-linear segment on the guidewire or, depending on the stiffness and frictional characteristics of the guidewire and catheter, may be practiced without permanent deformation of the non-linear segment. In particular, it should be noted that a number of guidewires have been proposed and developed that are highly resistant to permanent deformation, including guidewires having a shaft formed from a superelastic alloy. One such alloy that has been proposed and used has been an alloy of nickel and titanium (nitinol). Guidewires embodying such superelastic characteristics are disclosed in a number of U.S. patents such as U.S. Pat. Nos. 4,925,445 issued May 15, 1990 and 5,243,996 issued Sep. 14, 1993, among others. Although such guidewires are highly flexible and kink-free, they nonetheless are stiffer longitudinally than the shaft of the catheter with which they are used. The invention may be practiced with such guidewires by constraining the guidewire (contained within the catheter shaft) in a non-linear path selected to present greater resistance to advancement of the guidewire along that path than is presented to the catheter. The particular non-linear path may be determined empirically and can be expected to vary as a function of the variables of the materials, cross-sectional dimensions and surface characteristics of the guidewire and the catheter as well as any other characteristics that effect the relative stiffness and frictional effects of the catheter and guidewire. Thus, when the non-linear path is defined by a number of rollers or the like, the number, location and radii defined by the rollers can be varied to achieve the desired effect. The non-linear path should be such as to enable the catheter to be drawn along that path but to resist advancement of the guidewire.

Figure 23:
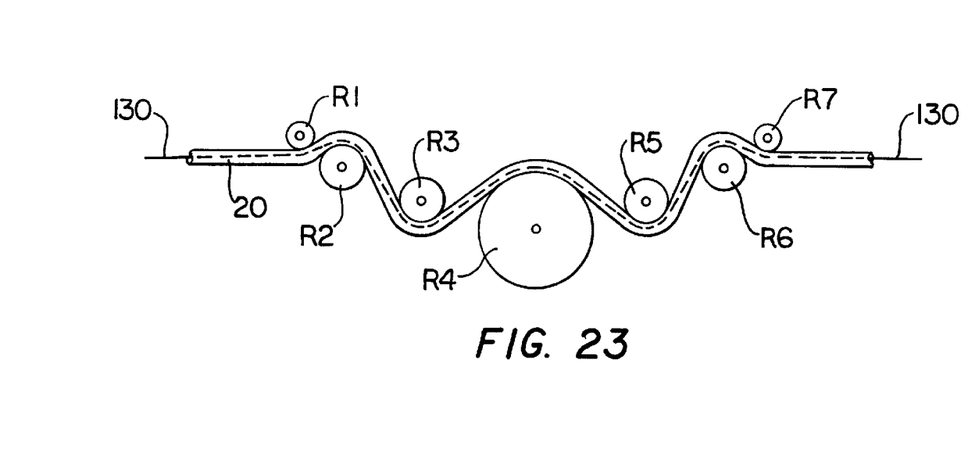
FIG. 23 is an illustration of a segment of catheter shaft and included guidewire in which the guidewire is elastically deformed to a non-linear configuration and in which the configuration is defined by a device defining a non-linear path sufficient to restrain the guidewire from movement while permitting the catheter to be advanced through the path by an over-the-guidewire.

FIG. 23 illustrates, somewhat diagrammatically, an arrangement of seven rollers R1–R7 that were used to enable a two lumen polyethylene catheter shaft 20 that contained a nitinol guidewire 130 (0.0137 inch diameter) in a manner that enabled the catheter shaft 20 to be withdrawn over the nitinol guidewire 130 while the guidewire remained stationary. In this embodiment it was found that seven rollers were required to define a more extensive serpentine-like, non-linear path than that which was found to be required when using a permanently deformed guidewire. Nonetheless, the array of seven rollers, including a relatively large main roller R-4 flanked by a plurality of smaller diameter rollers, or equivalent effectively constrained the guidewire without permanently deforming the guidewire yet which enabled the catheter to be stripped off of the guidewire. The outer surface of the guidewire was uncoated. Thus, the invention may be practiced by defining a non-linear path in which the catheter and included guidewire may be constrained to be either elastically or inelastically deformed. The precise configuration of the path will depend on the material and dimensions of the guidewire and catheter shaft.

It should be understood that the foregoing description of the invention is intended merely to be illustrative thereof and that other embodiments, modifications and equivalents may be apparent to those skilled in the art without departing from its spirit and principles.

Having thus described the invention, what we desire to claim and secure by Letters Patent is:

1. An elongate, substantially linear guidewire for use with a catheter, the guidewire comprising a free proximal end that, during use, remains external of the body of a patient into which the guidewire is inserted, a distal end, and a non-linear segment formed in the wire adjacent its proximal end, the non-linear segment including at least one permanent bend having at least a portion thereof displaced transversely from the longitudinal axis of the guidewire by a distance that is substantially greater than the diameter of the guidewire.

2. A guidewire as defined in claim 1 wherein the non-linear segment is defined by at least two bends formed in the guidewire.

3. A guidewire as defined in claim 2 wherein said at least two bends extend in reverse directions.

4. A guidewire as defined in claim 2 in which there are at least three bends arranged sequentially to be in successively reverse directions.

5. A guidewire as defined in claim 1 wherein the non-linear segment extends over a defined length and has a defined height, the ratio of the length to the height being no more than about ten.

6. A guidewire as defined in claim 1 wherein the non-linear segment is formed from a material having a different modulus of elasticity than the material from which the more distal portions of the guidewire shaft are formed.

7. A guidewire as defined in claim 6 wherein the non-linear segment is formed from a metal that includes tungsten.

8. A guidewire as defined in claim 1 wherein the guidewire comprises a shaft and where the non-linear segment is formed directly in the guidewire shaft.

9. A guidewire as defined in claim 1 wherein the guidewire is steerable.

10. A guidewire as defined in claim 9 wherein the guidewire comprises a percutaneous transluminal coronary angioplasty guidewire.

11. A guidewire as defined in claim 1 wherein the non-linear segment includes more then one permanent bend.

12. A guidewire as defined in claim 1 wherein said at least one permanent bend defines an included angle of between about 90° and 140°.

13. An attachment wire for the proximal end of a guidewire comprising:

a length of wire substantially shorter than the length of the guidewire, and a connector on at least one end of the attachment wire for connection to the proximal end of the guidewire, the attachment wire being deformable to have a non-linear segment.

14. An attachment as defined in claim 13 further comprising a connector on each end of the wire.

15. An attachment wire as defined in claim 14 wherein the connectors are of different construction.

16. An attachment wire as defined in claim 13 wherein the attachment wire has a non-linear segment formed therein.

17. An attachment wire as defined in either one of claims 15 or 16 wherein the wire has a proximal extremity and the non-linear segment is disposed distally of the proximal extremity of the attachment wire thereby to define a proximal tail segment of the attachment wire.

18. An attachment wire as defined in claim 13 wherein the wire is formed from a material having a higher modulus of elasticity than that from which the guidewire to which it is to be attached is formed.

19. An attachment wire as defined in claim 13 further comprising in combination. said guidewire connected to the attachment wire at the proximal the guidewire.

* * * * *